US012642883B2

(12) United States Patent
Gong et al.

(10) Patent No.: US 12,642,883 B2
(45) Date of Patent: Jun. 2, 2026

(54) INJECTABLE AND IN-SITU CROSSLINKING HYDROGEL FOR ENDOVASCULAR EMBOLIZATION

(71) Applicant: Wisconsin Alumni Research Foundation, Madison, WI (US)

(72) Inventors: Shaoqin Gong, Middleton, WI (US); Ruosen Xie, Madison, WI (US); Dai Yamanouchi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 635 days.

(21) Appl. No.: 17/952,056

(22) Filed: Sep. 23, 2022

(65) Prior Publication Data

US 2023/0105518 A1 Apr. 6, 2023

Related U.S. Application Data

(60) Provisional application No. 63/248,969, filed on Sep. 27, 2021.

(51) Int. Cl.

| | |
|---|---|
| ***A61L 24/04*** | (2006.01) |
| ***A61L 24/00*** | (2006.01) |
| ***A61L 24/02*** | (2006.01) |

(52) U.S. Cl.

CPC ......... *A61L 24/043* (2013.01); *A61L 24/0031* (2013.01); *A61L 24/02* (2013.01); *A61L 2400/04* (2013.01)

(58) Field of Classification Search

CPC .... A61L 24/043; A61L 24/0031; A61L 24/02; A61L 2400/04; A61L 24/001; A61L 2400/06; A61L 2430/32

See application file for complete search history.

(56) References Cited

PUBLICATIONS

Pal et al, Biomed. Mater, vol. 1, pp. 85-91 (Year: 2006).*

Hasany et al, Applied Materials Today (online Aug. 2021), vol. 24, pp. 1-20 (Year: 2021).*

Ooi et al, Biomacromolecules, vol. 19, pp. 3390-3400 (Year: 2018).*

Kharkar et al, ACS Biomater. Sci., Eng., Author manuscript; available in PMC Mar. 28, 2017, pp. 1-33 (Year: 2017).*

* cited by examiner

*Primary Examiner* — D. L. Jones

(74) *Attorney, Agent, or Firm* — Foley & Lardner LLP

(57) ABSTRACT

The present technology provides a composition comprising a mixture of a source of calcium ions, alginate conjugated to an acrylate monomer (ALG-A), carboxymethylcellulose conjugated to an acrylate monomer (CMC-A) and water, wherein the mixture is a shear-thinning gel. The compositions may further include a polythiol agent. Such compositions are injectable due to their shear-thinning properties, yet stay in place, undergo in situ crosslinking, and provide safe, simple and efficacious endovascular embolization. Methods of making and using such compositions are also provided.

28 Claims, 11 Drawing Sheets w/o covalent crosslinking with covalent crosslinking

INJECTABLE AND IN-SITU CROSSLINKING HYDROGEL FOR ENDOVASCULAR EMBOLIZATION

CROSS REFERENCE TO RELATED APPLICATION

This application claims the benefit of and priority to U.S. Patent Application No. 63/248,969, filed on Sep. 27, 2021, the contents of which are incorporated herein by reference in their entirety.

FIELD

The present technology relates generally to the field of endovascular embolization. Specifically, the present technology provides compositions, including shear-thinning hydrogels including ALG-A, CMC-A, a source of calcium ions, water and optionally a polythiol agent.

BACKGROUND

Endovascular embolization has been a standard of care and well-established technique to treat internal bleeding, aneurysm, and vascular malformation, in which an occlusive material or agent is delivered into the target vessel through the catheter.[1] Embolic materials can be categorized as solid materials (e.g., metallic coils) and liquid materials (e.g., Onyx™). Solid materials are considered to be effective in controlled and precise deployment into the target vessel, enabled by its radiopacity.[2] Solid materials are thus preferred for precise occlusion of small aneurysms and bleeding arteries caused by vascular injury. The major disadvantage of solid materials is that it is difficult to achieve complete thrombosis of the vessel.[3] Additionally, other complications can occur after embolization with metallic coils, including coil migration and coil compaction. These metallic coils can also produce extensive streak artifacts and thus cause interference of accurate follow-up assessment of the treated area with imaging techniques including fluoroscopy, computerized tomography (CT), and magnetic resonance imaging (MM). Particularly, for endovascular treatment of large aneurysms (e.g., abdominal aortic aneurysms), it is impractical to use metallic coils due to the lengthy and costly procedures required.[4] In contrast to solid embolic materials, the major advantage of liquid embolic materials is the quick inducement of thrombosis of the target vessel. Liquid materials can rapidly solidify after injection, and thus have the capability to occlude large vessels and arteriovenous malformations and manage endoleak during or after endovascular aortic aneurysm repair (EVAR).[5] However, liquid embolic materials are difficult to deploy in a controlled manner. They may incidentally embolize non-targeted vessels,[6] and/or cause dangerous entrapment of the delivering catheter which may lead to surgical difficulties.[7] Complications including recanalization and incomplete embolization can happen.

SUMMARY OF THE INVENTION

The present technology provides compositions that may be used to provide safe, consistent and controlled endovascular embolization. The compositions are capable of both non-covalent and covalent crosslinking over medically relevant time periods. Thus, they provide injectable hydrogels that stay put once placed and do not diffuse out of the vessel. Once injected, the compositions undergo covalent crosslinking in situ to provide mechanically stable embolisms. As such they may be used for the treatment of for the treatment of internal bleeding, aneurysm, and vascular malformation, among other conditions.

The present compositions include a mixture of a source of calcium ions, alginate conjugated to an acrylate monomer (ALG-A), carboxymethylcellulose conjugated to an acrylate monomer (CMC-A) and water, wherein the mixture is a shear-thinning gel. The compositions may further include a polythiol agent, and optionally, a thiol-ene crosslinking catalyst. The latter composition, over time, yields a crosslinked hydrogel that is biocompatible and mechanically stable.

In another aspect, the present technology provides methods of making the present compositions that include mixing alginate conjugated to an acrylate monomer (ALG-A), carboxymethylcellulose conjugated to an acrylate monomer (CMC-A) and a source of calcium ions in water to provide a shear-thinning gel. The methods may further include mixing a polythiol, and optionally a thiol-ene crosslinking catalyst, with ALG-A, CMC-A and the source of calcium ions in water.

In another aspect, the present technology provides methods of treatment comprising administering an effective amount of a composition of any embodiment disclosed herein to a subject in need thereof. In any embodiments, the subject is human. In any embodiments the subject is suffering from one or more of internal bleeding, aneurysm, and vascular malformation.

BRIEF DESCRIPTION OF THE DRAWINGS

FIGS. 3A-3D present results of rheological studies delineating the viscoelastic properties of the present compositions having solely non-covalent crosslinks with respect to the storage moduli (G') (top curve starting at left) and loss moduli (G") (bottom curve starting at left). FIG. 3A: The strain sweep (strain: 0.01%-500%, frequency: 0.1 Hz, 37° C.) suggests that the G' exceeded G" at small strains, indicating dominant elastic behavior. As the strain increased, G' and G" decreased, eventually intersecting at a crossover strain (51.9%), and beyond this strain, G" exceeded G', indicating a dominant viscous response. FIG. 3B: Recovery of the hydrogel under alternating high and low strain conditions (100% strain and 0.1% strain (right Y-axis), frequency: 0.1 Hz, 37° C.) was studied, which demonstrated the capability of the hydrogel to recover its stability and integrity after injection.

FIG. 3C: The shear rate sweep reveals the viscosity of the hydrogel decreased as the shear rate increased, demonstrating its shear-thinning behavior before in situ covalent crosslinking. FIG. 3D: The frequency sweep (0.01-63.1 Hz, strain: 0.1%, 37° C.) indicates viscoelastic solid-like behavior of the hydrogel. FIG. 3E: The in situ covalent crosslinking kinetics of an illustrative composition including both non-covalent and covalent crosslinking (i.e., an embodiment of the DCN hydrogel) at 37° C. was studied by measuring the changes of G' and G". Both G' and G" of the DCN hydrogel were gradually increased over time and the increments reached plateaus after ~45 min, indicating complete thiol-ene reactions. FIG. 3F: The mechanical behavior of the DCN hydrogel was investigated by measuring the stress-strain curve. FIG. 3G-31I: The microstructures of the hydrogel without and with covalent crosslinking were observed by SEM. Scale bar: 20 μm.

FIG. 4A is a graph showing the extent of hemolysis of human red blood cells in the presence of commercially available embolic agents (Onyx™), DCN hydrogel and PBS (n=3). FIG. 4B shows the radiopacity of saline (in a 1.7-mL Eppendorf tube, negative control), DCN hydrogel (loaded with 21 wt % Iohexol, in a 1.7-mL Eppendorf tube) and a metallic stent graft (positive control), measured by X-ray. FIG. 4C shows a quantitative analysis of radiopacity for the three different compositions, with the stent graft showing a varying radiopacity, the saline showing a broad but low radiopacity and the DCN hydrogel showing a broad but higher radiopacity than the saline.

FIG. 4D shows the cell viability of the components used to form DCN hydrogel (Alg-MA, CMC-MA and $CaSO_4$) and DCN hydrogel on NIH 3T3 fibroblasts. Statistical significance was calculated via one-way ANOVA with a Tukey's post hoc test. ns, not significant. n.d., not detected.

FIG. 5A shows a schematic representation of the rabbit arterial occlusion model. FIG. 5B shows a representative image of the DCN hydrogel-injected artery after embolization. FIG. 5C shows H&E staining and FIG. 5D shows Masson's trichrome staining that were performed, to evaluate artery embolization efficacy. Sections were collected from the arteries injected with saline, Onyx™ or DCN hydrogel in a rabbit model at different time point (n=3 for each time point) post-treatment. Onyx™ was shown as black spots. The DCN hydrogel was shown as light purples in H&E staining and light purple in Masson's trichrome staining. Scale bars: 400 μm (low magnification, 5×) and 100 μm (high magnification, 20×). Lumen (L), media (M), and adventitia (A) were labeled.

FIG. 6 shows representative results of immunohistochemistry staining of the embolized rabbit arteries performed to assay macrophages (MAC387), proliferating cells (PCNA) and cell apoptosis (TUNEL) in the treated arteries, respectively. Sections were collected from the arteries injected with saline, Onyx™ and DCN hydrogel in a rabbit model at different time point (n=3 for each time point) post-treatment. Scale bars: 400 μm (low magnification, 5×) and 100 μm (high magnification, 20×).

FIG. 7 shows the $^1H$ NMR spectrum of 2-aminoethyl methacrylate hydrochloride in $D_2O$ at 400 MHz.

FIG. 8 shows the $^1H$ NMR spectrum of alginate methacrylate (ALG-MA) in $D_2O$ at 400 MHz. It will be appreciated that the chemical structure in this figure is schematic and not actual; ALG-MA may be a random copolymer or a block copolymer.

FIG. 9 shows the $^1H$ NMR spectrum of carboxy methyl cellulose methacrylate (CMC-MA) in $D_2O$ at 400 MHz. It will be appreciated that the chemical structure in this figure is schematic and not actual; CMC-MA may be a random copolymer or a block copolymer.

DETAILED DESCRIPTION

Figure 1:
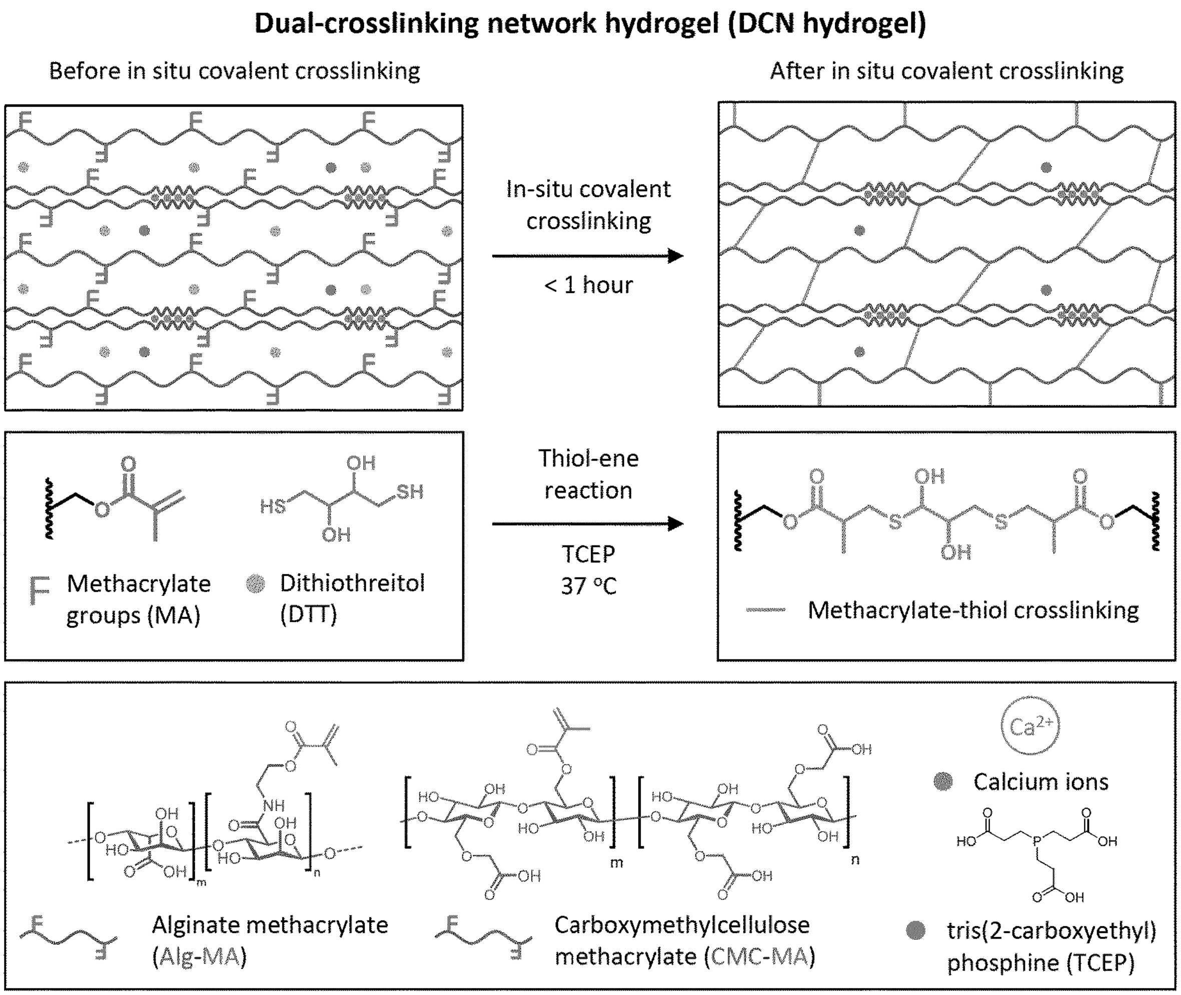
FIG. 1 is a schematic of illustrative embodiments of the present compositions, including a composition for a non-covalent crosslinked hydrogel comprising alginate-methacrylate (ALG-MA), carboxymethylcellulose methacrylate (CMC-MA) and calcium ions; a dual crosslinked hydrogel, from a composition further including an illustrative polythiol agent that undergoes thiol-ene reaction to provide covalent crosslinking of the composition; and schematics of illustrative structures of ALG-MA, CMC-MA and related components of the present compositions.

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term. In any embodiments, "about" may also mean up to ±1%, ±2%, or ±5% of the particular term.

As used herein, "alkyl groups" include straight chain and branched chain alkyl (or alkylene) groups having 1-18 carbon atoms and therefore includes alkyl groups with any of 1, 2, 3, 4, 5, 6, 7, 8, 9, 10, 11, 12, 1.3, 14, 15, 16, 17, or 18 carbon atoms. Thus, in any embodiments, the alkyl group (which may also be an alkylene group) may have 2-18, 1-12, 2-12 1-6, or 2-6 carbons. Examples of straight chain alkyl groups include groups such as methyl, ethyl, n-propyl, n-butyl, n-pentyl, n-hexyl, n-dodecyl, and n-octadecyl. Examples of branched alkyl groups include, but are not limited to, isopropyl, iso-butyl, sec-butyl, tert-butyl, neopentyl, isopentyl, and 2,2-dimethylpropyl groups. Alkyl groups are unsubstituted unless otherwise indicated, e.g., substituted with ether, amine, hydroxyl, thiol, carboxy and the like.

As used herein, a "subject" is a mammal, such as a cat, dog, rodent, pig, horse, cow, or primate. In any embodiments, the subject is a human.

In one aspect, the present technology provides compositions including a mixture of a source of calcium ions, alginate conjugated to an acrylate monomer (ALG-A), carboxymethylcellulose conjugated to an acrylate monomer (CMC-A) and water, wherein the mixture is a shear-thinning gel.

The present compositions include a source of calcium ions. Generally, the source may be a water soluble (i.e., solubility greater than 1 mM at 25° C.) calcium salt, e.g., an inorganic calcium salt such as calcium sulfate or calcium chloride, or a calcium salt of a water-soluble organic compound, e.g., calcium acetate, calcium citrate, calcium gluconate, or calcium lactate. The source of calcium ions may also include mixtures of any two or more of the foregoing. The composition may have 0.1 wt % to 10 wt % of a source of calcium ions, e.g., 0.1, 0.2, 0.3, 0.4, 0.5, 0.6, 0.8, 1.0, 1.25, 1.5, 1.75, 2.0, 2.5, 3, 3.5, 4, 4.5, 5, 5.5, 6, 6.5, 7, 8, 9, or 10 wt % of a source of calcium ions or a range between and including any two or the foregoing values. For example, the compositions may have 0.2 wt % to 2 wt % or 0.4 wt % to 1.6 wt % of a source of calcium ions, including but not limited to any listed herein.

The present compositions include ALG-A and CMC-A. A range of amounts of ALG-A may be used e.g., 0.5 to 10 wt % ALG-A. Thus, the compositions may include 0.5, 1, 1.5, 2, 2.5, 3, 3.5, 4, 4.5, 5, 5.5, 6, 6.5, 7, 7.5, 8, 9, 10 wt % ALG-A, or a range between and including any two of the foregoing values such as 1 wt % to 8 or 10 wt %, or 2 wt % to 6 wt % ALG-A. Similarly, a range of amounts of CMC-A may be used e.g., 0.5 to 20 wt % CMC-A. Thus, the compositions may include 0.5, 1, 1.5, 2, 2.5, 3, 3.5, 4, 4.5, 5, 5.5, 6, 6.5, 7, 7.5, 8, 9, 10, 11, 12, 14, 16, 18, 20 wt % CMC-A, or a range between and including any two of the foregoing values such as 1 wt % to 8 wt %, 1 wt % to 10 wt %, or 2 wt % to 6 wt % CMC-A.

The alginate in ALG-A may have a weight average molecular weight of from 100 kDa to 2,000 kDa. For example, 100, 200, 300, 400, 500, 600, 700, 800, 1,000, 1,200, 1,500, 1,800, or 2,000 kDa or a range between and including any two of the foregoing values, e.g., 500 kDa to 2,000 kDa. Likewise, the carboxymethylcellulose of the CMC-A may have a weight average molecular weight of from 100 kDa to 2,000 kDa, including for example 100, 200, 300, 400, 500, 600, 700, 800, 1,000, 1,200, 1,500, 1,800, or 2,000 kDa or a range between and including any two of the foregoing values, e.g. 100 kDa to 500 kDa. The weight average molecular weight of ALG-A or CMC-A may be estimated from the viscosities of each as determined using methods known to those of skill in the art.

The acrylate monomer of ALG-A, CMC-A or both may be acrylate or methacrylate, i.e.,

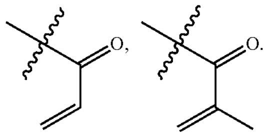

The acrylate monomer may further include a linking group, e.g., 0 or NH group such that the acrylate monomer is an ester or amide. The linking group may also be a short chain such as an aminoalkyl or oxyalkyl chain where the alkyl group has 1-18 carbon atoms, e.g. 1, 2, 3, 4, 5, 6, 7, 8, 9, 10, 12, 14, 16, or 18 carbon atoms or a range between any two of the foregoing values. In any embodiments then, the acrylate monomer of ALG-A, CMC-A or both may comprise an aminoalkyl acrylate or aminoalkyl methacrylate. In any embodiments, the acrylate monomer of ALG-A, CMC-A or both is 2-aminoethylacrylate or 2-aminoethylmethacrylate. FIG. 1 shows a schematic of an illustrative embodiment of the present technology, showing how the acrylate monomer may be attached to ALG and CMC.

The substitution level of the ALG or the CMC with the acrylate monomer may vary. Herein, "substitution level" refers to the percentage of repeating units in the ALG or the CMC that have been substituted by acrylate. For example, ALG-A may have a substitution level of 10-30% acrylate monomer with respect to the number of repeating units of alginate, including e.g., 10, 11, 12, 13, 14, 15, 16, 17, 18, 19, 20, 21, 22, 23, 24, 25, 26, 27, 28, 29, or 30%, or a range between and including any two of the foregoing values. Thus, ALG-A may have a substitution level of, e.g., 12-24% or 15-21%. Similarly, CMC-A may have a substitution level of 15-35% acrylate monomer with respect to the number of repeating units of carboxymethylcellulose, including e.g., 15, 16, 17, 18, 19, 20, 21, 22, 23, 24, 25, 26, 27, 28, 29, 30, 31, 32, 33, 34, or 35%, or a range between and including any two of the foregoing values. Thus, CMC-A may have a substitution level of, e.g., 20-35% or 24-30%.

The weight ratio of ALG-A:CMC-A may vary in the present compositions. For example, the weight ratio may range from 1:2 to 2:1, or from 2:3 to 3:2, or may be about 1:1.

In any embodiments, the composition may include a pharmaceutically acceptable buffering agent for pH adjustment. Pharmaceutically acceptable buffering agents are those which, within the scope of sound medical evaluation, are suitable for use in contact with the tissues and organs of subjects, including human subjects, without displaying toxicity, irritation, allergic response and the like and are commensurate with a reasonable benefit/risk ratio. For example, pharmaceutically acceptable buffering agents may not cause deleterious precipitation of the calcium salts used in the present compositions or found in blood. In any embodiments the pharmaceutically acceptable buffering agent may be a pharmaceutically acceptable amine. In any embodiments, the pharmaceutically acceptable buffering agent may be triethanolamine, 2-amino-2-(hydroxymethyl)-1,3-propanediol (Tris), and 2-amino-2-methyl-1,3-propandiol.

The present compositions may include a polythiol agent (one with two or more thiol groups). The polythiol agent of the present technology is capable of crosslinking the ALG-A and CMC-A by undergoing a thiol-ene reaction (Michael addition) with the acrylate groups. It is to be understood that by crosslinking, covalent linkages between molecules of ALG-A, CMC-A and/or both are formed with the polythiol agent. In any embodiments, the polythiol agent may be a polymer, e.g., a PEG with terminal thiols, including branched PEGS terminal thiols. Such polymers may have a weight average molecular weight of 200 Da to 20 kDa. In any embodiments, the polythiol may be a small organic molecule (e.g., not a polymer) that has a molecular weight of not more than 500 Da. In any embodiments the polythiol agent bears two, three or four thiol groups. In any embodiments, the polythiol agent is a dithiol agent. In any embodiments, the polythiol agent may be selected from the group consisting of dithiothreitol, dithioerythritol, propane-1,3-dithiol, meso-2,3-dimercaptosuccinic acid, dimercaprol, dihydrolipoic acid, trimethylolpropane tris(3-mercaptopropionate), pentaerythritol tetrakis(3-mercaptopropionate), poly(ethylene glycol) with two terminal thiols, and 4-arm poly(ethylene glycol) with four terminal thiols. In any embodiments the polythiol may be a poly(ethylene glycol) with two terminal thiols. Such polythiols may have weight average molecular weights of 200 Da to 20 kDa, including 200, 200, 300, 400, 500, 600, 800, 1000, 1500, 2000, 3000, 3500, 4000, 5000, 6000, 8000, 10000, and 20000 Da, or a range between and including any two of the foregoing values. In any embodiments, the polythiol may be a poly (ethylene glycol) with four terminal thiols. Such polythiols may have weight average molecular weights of 400 Da to 20 kDa, including 400, 600, 800, 1000, 1500, 2000, 3000, 4000, 5000, 6000, 8000, 10000, and 20000 Da, or a range between and including any two of the foregoing values. In any embodiments the composition may include 0.1 to 2 molar equivalents of thiol groups on the polythiol agent to acrylate or methacrylate groups on ALG-A. For example, the composition may include 0.5, 0.6, 0.7, 0.8, 0.9, 1, 1.1, 1.2, 1.3, 1.4, 1.5, 1.6, 1.7, 1.8, 1.9, or 2 molar equivalents or a range between and including any two of the forgoing values such as 0.5 to 1.5 or 0.8 to 1.2 molar equivalents of thiol groups on polythiol agent to meth/acrylate groups on ALG-A. In any embodiments, the composition may include about 1 molar equivalent of thiol groups on polythiol agent to meth/acrylate groups on ALG-A.

For compositions including a polythiol agent, a thiol-ene crosslinking catalyst may optionally be included. The thiol ene-crosslinking catalyst catalyzes the thiol-ene reaction between the polythiol agent and the ALA-A and/or CMC-A. In any embodiments, the thiol-ene crosslinking catalyst may be a reducing agent, e.g., tris(2-carboxyethyl)phosphine. In any embodiments, the compositions may include 0.1 mM to 100 mM thiol-ene crosslinking catalyst. For example, the compositions may include 0.1, 0.5, 1, 1.5, 2, 2.5, 3, 3.5, 4, 4.5, 5, 10, 15, 20, 30, 40, 50, 60, 70, 80, 90, or 100 mM or a range between and including any two of the foregoing values.

It will be understood by those of skill in the art that the compositions disclosed herein take several forms. In any embodiments, the compositions are shear-thinning hydrogels that are suitable for injection. Such hydrogels may be crosslinked, e.g., they may primarily have non-covalent crosslinks between the ALG-A mediated by calcium ions. The hydrogels may also have covalent crosslinks formed by the polythiol agent via a thiol-ene reaction with the ALG-A and/or CMC-A. In any embodiments, the composition may exhibit a viscosity of at least 1,000 Pas at a shear rate of 0.1/s. In any embodiments, the composition may exhibit a viscosity of at least 10,000 Pas at a shear rate of 0.1/s. In any embodiments, the composition may exhibit a viscosity of less than 100 Pas at a shear rate of 20/s. In any embodiments, the composition may exhibit a viscosity of less than 20 Pas at a shear rate of 20/s. In any embodiments, the composition exhibits a storage modulus (G') greater than the loss modulus (G") at strains of less than 50% when measured at a fixed frequency of 0.1 Hz and a temperature of 37° C. In any embodiments, the composition may exhibit a Young's modulus of about 4 to about to 8 kPa, e.g., about 5 to 6 kPa or about 5.7 kPa.

In another aspect, the present technology provides methods of making a composition herein including mixing alginate conjugated to an acrylate monomer (ALG-A), carboxymethylcellulose conjugated to an acrylate monomer (CMC-A) and a source of calcium ions in water to provide a shear-thinning gel. The methods may further include mixing a polythiol, and optionally a thiol-ene crosslinking catalyst, with ALG-A, CMC-A and the source of calcium ions in water. It will be understood that the methods include using any of the ALG-A, CMC-A, calcium ion source, polythiol agent and thiol-ene crosslinking catalyst disclosed herein in any embodiment of the compositions.

In another aspect, the present technology includes methods of treatment including administering an effective amount of a composition of any embodiment disclosed herein to a subject in need thereof. In any embodiments, the subject is human. In any embodiment, the subject is suffering from one or more of internal bleeding, aneurysm, and vascular malformation. The compositions may be administered by injection into a target blood vessel. In any embodiments, the internal bleeding is caused by a bleeding artery and the target blood vessel is the bleeding artery.

The examples herein are provided to illustrate advantages of the present technology and to further assist a person of ordinary skill in the art with preparing or using the compositions of the present technology. To the extent that the compositions include ionizable components, salts such as pharmaceutically acceptable salts of such components may also be used. The examples herein are also presented in order to more fully illustrate certain aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology

EXAMPLES

General Methods

Cell culture: NIH 3T3 fibroblasts were cultured at 37° C. in a 5% $CO_2$ atmosphere with the Dulbecco's Modified Eagle Medium (Thermo Fisher Scientific) supplemented with 10% (v/v) fetal bovine serum (Thermo Fisher Scientific) and 1% (v/v) Penicillin-Streptomycin (Thermo Fisher Scientific). RAW 264.7 macrophages were cultured at 37° C. in a 5% $CO_2$ atmosphere with the RPMI 1640 Medium (Thermo Fisher Scientific) supplemented with 10% (v/v) fetal bovine serum (Thermo Fisher Scientific) and 1% (v/v) Penicillin-Streptomycin (Thermo Fisher Scientific).

Animals: All animal experiments were performed following the biosafety protocol and the animal protocol approved by Kawasumi Laboratories, Inc. Japanese white rabbits (male and female, body weight 2.0-3.0 kg, Slc:JW/CSK, supplied by Japan SLC, Inc.) were randomly divided into 9 groups (3 treatments (i.e., saline, Onyx or DCN hydrogel)×3 time points (i.e., 1 day, 1 week and 1 month); n=3 per group and thus 27 rabbits total for this study) for the following experiments.

Statistical analysis: Results are presented as mean±standard deviation. Statistical differences between experimental groups were analyzed using a one-way ANOVA test followed by Tukey's post hoc comparison test. Statistical analyses were performed using GraphPad Prism software. Significant differences between groups were indicated by *p<0.05, p<0.01, *p<0.001 and ****p<0.0001, respectively. p≥0.05 was considered to be not statistically significant in all analyses (95% confidence level).

Example 1—Preparation of Hydrogels

Figure 7:
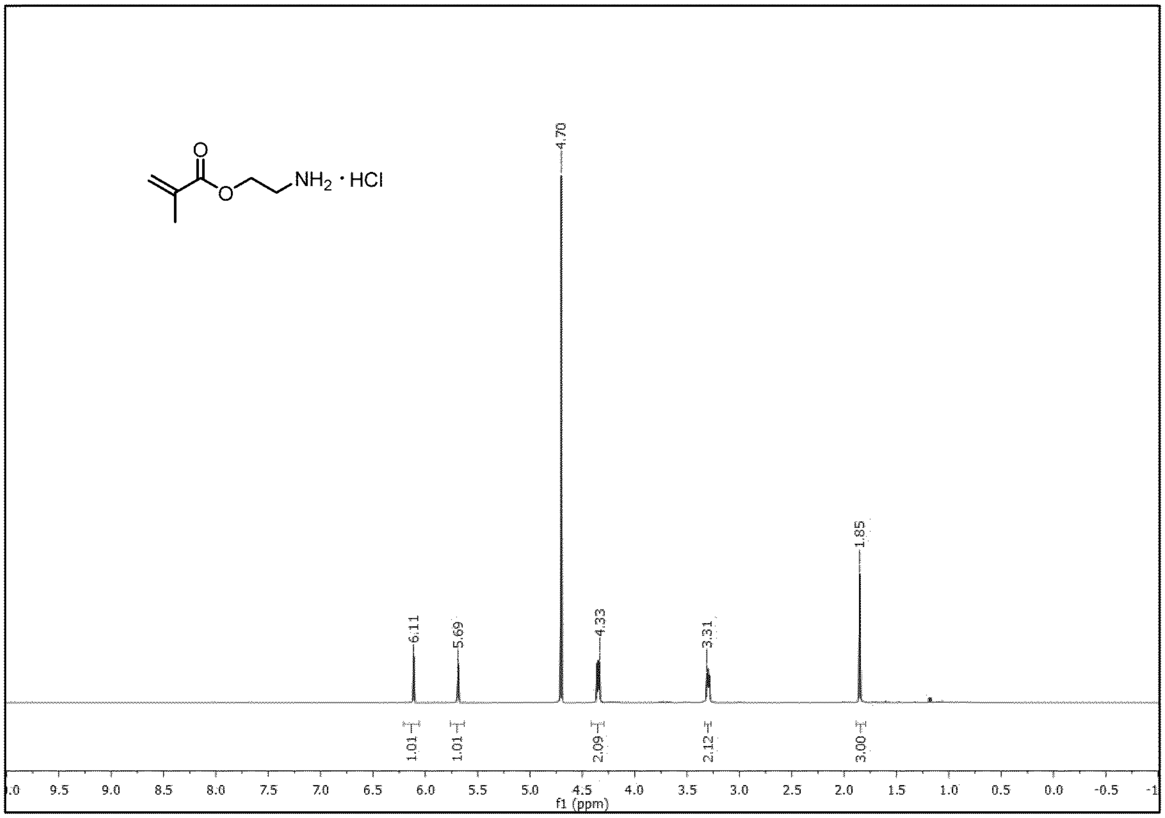

Synthesis of AMA·HCl: 2-Aminoethyl methacrylate hydrochloride (AMA·HCl) was synthesized using a previously reported protocol[17]. Ethanolamine hydrochloride (13.0 g, 0.13 mol), methacryloyl chloride (20.0 mL, 0.19 mol), and hydroquinone (0.13 g, 1.2 mmol, as an inhibitor to avoid polymerization) were added to a three-necked round bottomed flask fitted with a condenser. Ethanolamine hydrochloride salt was melted at 95° C. under nitrogen for 1 h, and the reaction was maintained at 70° C. for 2 h. Hydrogen chloride gas formed during the reaction was neutralized with 1M NaOH aqueous solution connected to the flask. The crude product was cooled to 40° C., diluted with tetrahydrofuran (12.5 mL), and precipitated into n-pentane (100 mL). The resulting creamy white precipitate was isolated by centrifugation at 1,000×g, washed thoroughly with ice-cold n-pentane (100 mL), and dried under vacuum. The crude product was then recrystallized twice using a 7:3 ethyl acetate/isopropanol mixture. The purified product AMA·HCl was dried under vacuum and characterized by $^1$H-NMR (deuterium oxide, 400 MHz, FIG. 7).

Figure 8:
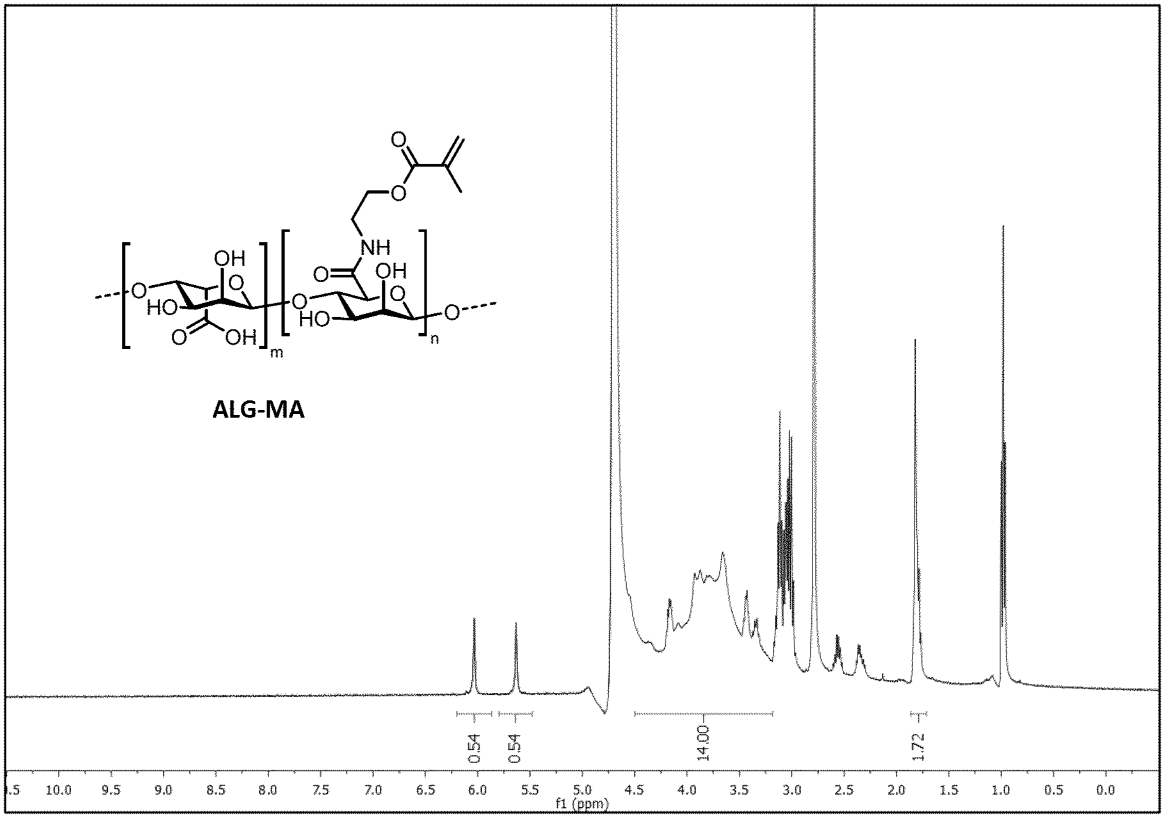

Synthesis of alginate methacrylate (Alg-MA): Alg-MA was synthesized through an amidation reaction[18]. In brief, sodium alginate (2.50 g, 12.5 mmol or 1 equiv. of carboxyl groups) was dissolved in 50 mM MES buffer (pH=6.0)

containing 0.5 M NaCl to yield a 1 wt % solution. EDC·HCl (1.20 g, 0.5 equiv.) and NHS (0.36 g, 0.25 equiv.) were introduced into the mixture. After 5 min, AMA·HCl (0.52 g, 0.25 equiv.) was added to the solution and the reaction was stirred at 20° C. for 24 h. Thereafter, the mixture was dialyzed against ultrapure water (molecular weight cut-off, MWCO=12-14 kDa) for 3 days, filtered through a 0.22-μm membrane and finally lyophilized. The purified product Alg-MA was characterized by $^1$H-NMR (deuterium oxide, 400 MHz, FIG. 8), and showed a 27% substitution level of the methacrylate.

Figure 9:
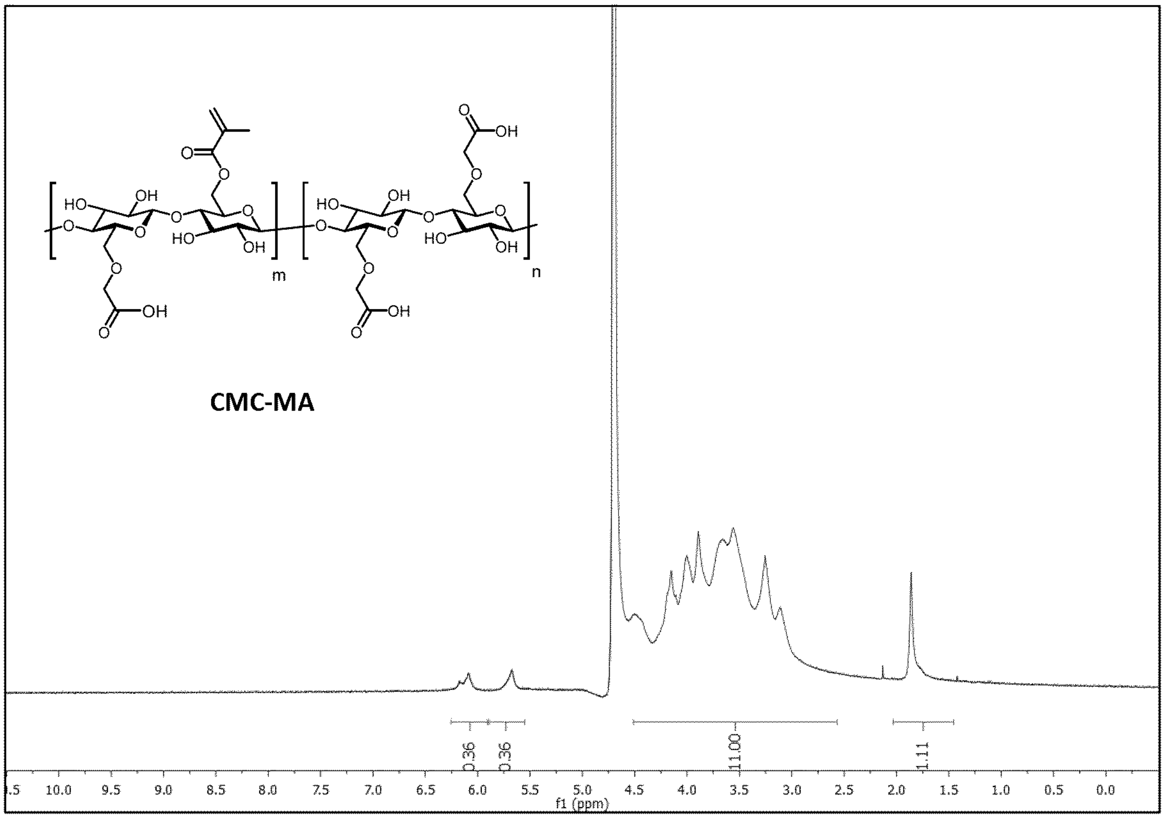

Synthesis of carboxymethylcellulose methacrylate (CMC-MA): CMC-MA was prepared through the conventional methacrylic anhydride route[9b]. CMC (2.50 g, 6.3 mmol or 1 equiv. of (3-hydroxyl groups) was dissolved in 125 mL ultrapure water and cooled on ice to yield a 2 wt % solution. The pH was adjusted to ~9.0 by adding 6 g (10 equiv.) sodium carbonate and 5M NaOH aqueous solution. Methacrylic anhydride (8.30 mL, 10 equiv. of total (3-hydroxyl groups) was added to the solution and the pH was maintained around pH 8.0 by adding a certain amount of 5M NaOH aqueous solution. The reaction was carried out at room temperature with vigorous stirring for 12 hours. The modified CMC was precipitated with 500 mL of acetone to remove the remaining methacrylic anhydride and other byproducts. The precipitate was collected and rehydrated in ultrapure water, dialyzed against ultrapure water (MWCO=12-14 kDa) for 3 days, filtered through a 0.22-μm membrane and finally lyophilized. The purified product CMC-MA was characterized by $^1$H-NMR (deuterium oxide, 400 MHz, FIG. 9, which showed an 18% substitution level of the methacrylate.

Preparation of dual-crosslinking network (DCN) hydrogels: Two steps were involved for the preparation of DCN hydrogel: (1) the formation of injectable hydrogels, and (2) the addition of in situ covalent crosslinking reagents. First, the lyophilized Alg-MA and CMC-MA were dissolved in 50 mM triethanolamine buffer (pH=8.5) by mechanical stirring at 100 rpm for 24 h. A slurry containing 240 mg/mL $CaSO_4 \cdot 2H_2O$ ($CaSO_4 \cdot 2H_2O$/Alg-MA=1/5, wt/wt) was added dropwise into the polymer solution, and mechanically stirred for another 24 h. The resulting injectable hydrogel was collected for storage at 4° C. Second, the in situ covalent crosslinking reagents were added to the injectable hydrogel prior to animal injections. Specifically, DTT (100 mg/mL, final DTT/methacrylate groups=1/1, mol/mol) and TCEP (100 mg/mL, final concentration at 2.5 mM in the DCN hydrogel) solutions were added to the injectable hydrogels. The hydrogel was thoroughly mixed by a spatula and adjusted to pH 8.5 by adding an appropriate amount of 2M NaOH solution. The mixture was then loaded into a Luer-Lok syringe using a spatula or syringe plunger and warmed at 37° C. before injections.

FIG. 1 shows a schematic illustration of an illustrative embodiment of the present hydrogel before and after in situ covalent crosslinking. Covalent crosslinking is due to the thiol-ene reaction of DTT (a polythiol) with two methacrylate groups. Non-covalent crosslinking mediated by calcium ions shown by squiggles and dots. The bottom panel shows examples of attachment points of methacrylate on alginate and carboxymethylcellulose. The thiol-ene reaction in the as-prepared hydrogel can be halted at 4° C. for more than one hour without inducing premature crosslinking or impacting its in situ covalent crosslinking capability, thereby providing a time window for surgical operation. Right before use, the pre-mixed DCN hydrogel was warmed at 37° C. Thereafter, upon deployment, the body temperature at 37° C. triggered in situ thiol-ene reactions between DTT and the methacrylate groups on Alg-MA and CMC-MA, leading to a covalently crosslinked tough hydrogel within one hour after deployment.

Example 2—Characterization of Hydrogel Physical Properties

Rheology: All rheological measurements were performed using an AR2000 rheometer (TA instruments) with an environmental test chamber to maintain the temperature at 37° C., following reported protocols[4, 19]. All hydrogel samples were cast between a 25-mm diameter stainless steel upper plate and a lower Peltier plate with the gap between plates at 1.0 mm for all measurements. Examination of the hydrogel without in situ covalent crosslinking was performed by oscillatory strain sweeps (1.0 Hz, 0.1-500% strain), and frequency sweeps (0.01-63 Hz, 0.5% strain, in the linear viscoelastic region). The shear rate sweep was conducted to study the shear-thinning behavior. Thixotropic test was performed at 1.0 Hz under strain oscillation between 0.1% for 2 minutes and 100% for 2 minutes. For the DCN hydrogel undergoing in situ covalent crosslinking, the crosslinking kinetics was observed in situ via time sweeps (1.0 Hz, 0.1% strain).

Tensile test: The DCN hydrogel was cast in a dumbbell-shaped (ASTM D638 Type V) mold at 37° C. overnight. The tensile tests were carried out using a pre-tension of 0.1 N and an extension rate of 10 mm $min^{-1}$ (Instron, 5848, 10 N load cell). Young's modulus, elongation at break, and ultimate tensile strength were recorded.

Injectability: The DCN hydrogel was loaded into a 1-mL or 3-mL Luer-Lok syringes (BD Biosciences) using a spatula or syringe plunger before injections. Several types of needles (BD Biosciences) and a 6-French catheter (Cook Medical LLC) were connected to the syringe, respectively. The injection forces were measured by Instron testing machines. The injection flow rates were set at 0.1 mL/min or 1 mL/min.

Scanning electron microscopy (SEM): An SEM (Zeiss LEO 1530-1) was used to visualize the hydrogel microstructures with or without in situ covalent crosslinking. The hydrogel without in situ covalent crosslinking was prepared following the procedure used to prepare the DCN hydrogel but without the addition of DTT and TCEP. The DCN hydrogel was prepared and incubated at 37° C. overnight to allow covalent crosslinking. Thereafter, hydrogel samples were flash-frozen in liquid nitrogen, cut into small pieces, and subsequently lyophilized (<0.1 mBar, and −80° C., Labconco). The cross-sections of the lyophilized samples were then sputter-coated with 7 nm gold (Leica EM ACE600) and observed by SEM.

Discussion Even without in situ covalent crosslinking, the hydrogel crosslinked with only the alginate-calcium coordination interaction was visually observed as a solid hydrogel instead of a liquid polymer solution. It was able to stay at the bottom of a centrifuge tube which was placed upside down for 7 days at 20° C. without flowing down, and was still injectable thereafter.

Figure 2A:
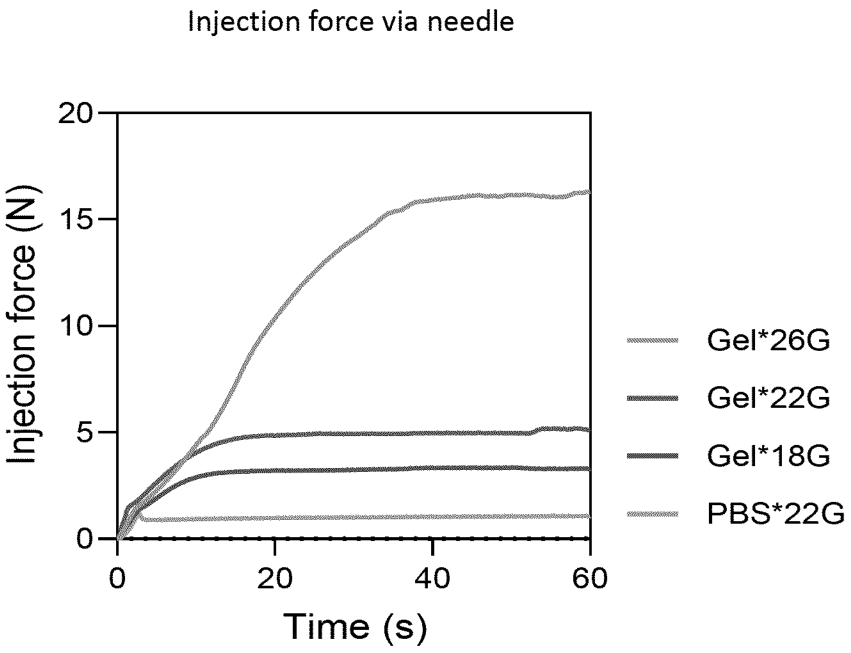
FIGS. 2A-2B shows the injection force needed to push an illustrative embodiment of the present compositions (non-covalent crosslinking only) through (FIG. 2A) different size needles and through (FIG. 2B) a catheter at different speeds and volumes.
Figure 2B:
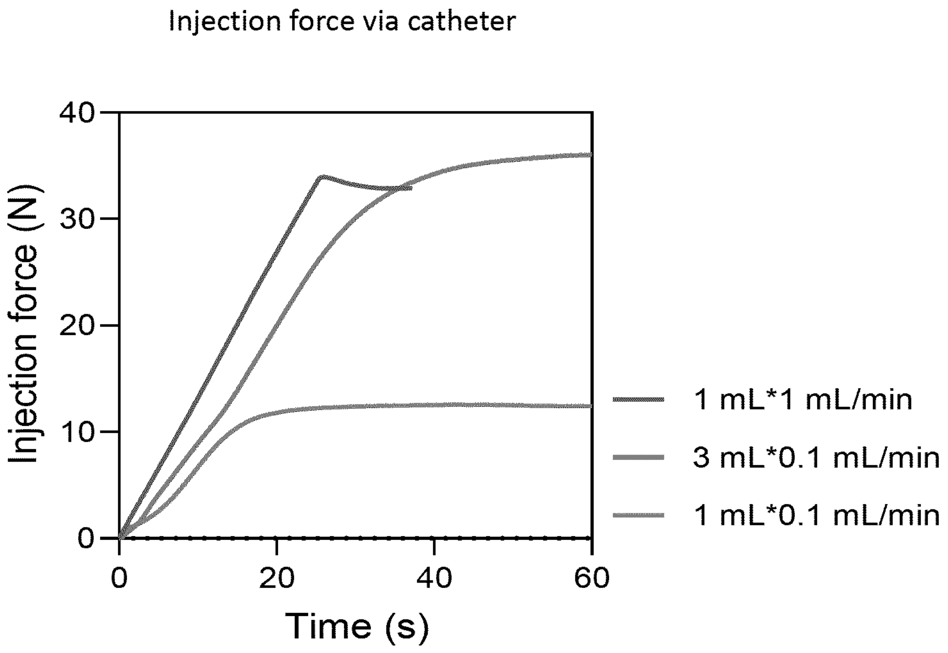

The injectability of the DCN hydrogel was first investigated by manual injections. The DCN hydrogel can be injected easily via needles at 18-, 22-, and 26-gauge. It can also be smoothly injected with a single hand through a 6-French catheter that is 1.25 meters long, which is used clinically for endovascular surgeries in patients. To quantitatively study the influence of injection conditions on the injection force required for the DCN hydrogel, the injection forces under different injection conditions were measured using a mechanical tester by varying the size of the needle, the rate of injection, and the volume of the syringe. Under a specific set of injection conditions, the injection force increased linearly until it reached a plateau indicating the maximum force needed to extrude the DCN hydrogel from different types of needles or catheters. As expected, needles with smaller diameters required a higher force to inject the DCN hydrogel. It required 16.3 N for injection via a 26-gauge needle, but only 3.3 N via an 18-gauge one (FIG. 2A). For injection via a 6-French catheter, a higher injection rate led to a higher injection force (FIG. 2B). Using a 1-mL syringe, the DCN hydrogel required 12.4 N for injection at 0.1 mL/min, but 32.9 N for injection at 1.0 mL/min. The volume of the syringe for injection also mattered. When the injection rate was 0.1 mL/min, the force required to inject the DCN hydrogel with a 1-mL and a 3-mL syringe was 32.9 N and 36.0 N, respectively. Collectively, the forces needed to inject the DCN hydrogel were within the range that can be generated manually by a surgeon without the need for additional equipment, and the injection forces were tunable by varying injection conditions.

Figure 3A:
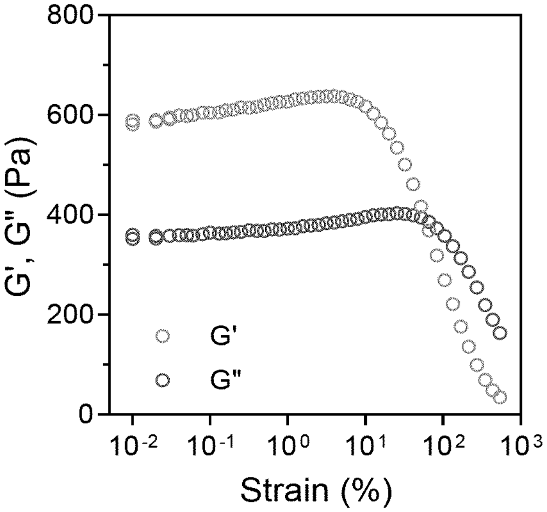
FIGS. 3A-3H show characterization test results of an illustrative embodiment of the present compositions (referred to as a "DCN hydrogel").
Figure 3B:
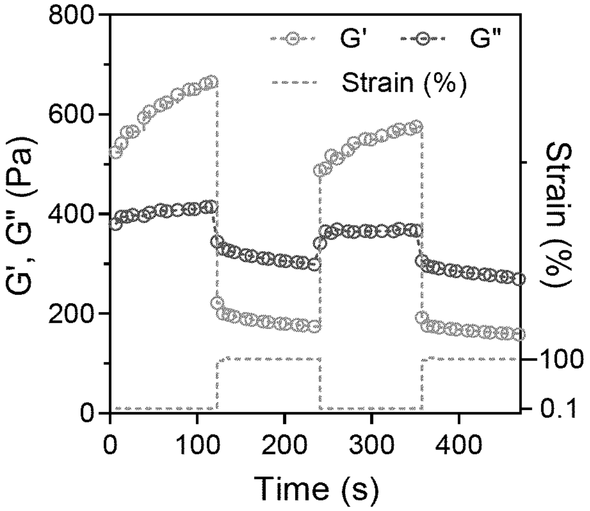
Figure 3C:
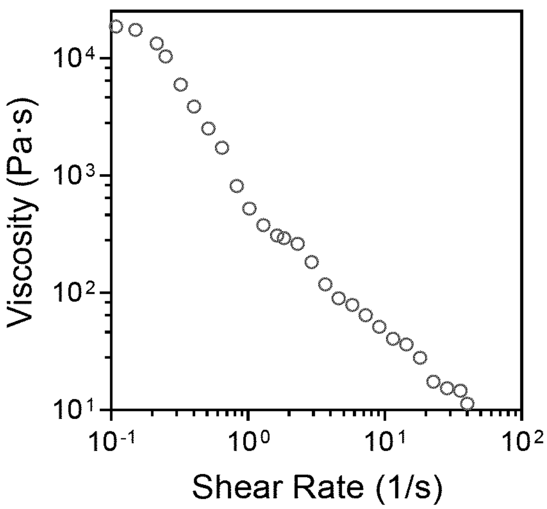
Figure 3D:
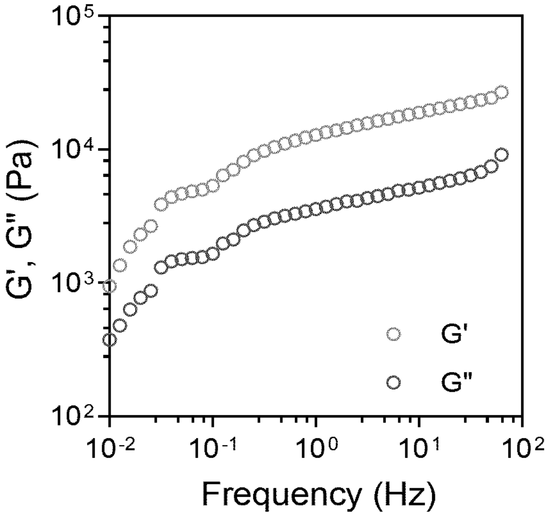

The viscoelastic property of the hydrogel without in situ covalent crosslinking was first investigated by a rheometer.[12] Representative results from large strain sweep experiments of the hydrogel measured at 0.1 Hz and 37° C. are shown in FIG. 3A. To investigate the non-linear viscoelasticity, the storage (G') and loss (G") moduli of the hydrogel were measured at a fixed frequency (FIG. 3A). The G' exceeded G" at small strains, indicating dominant elastic behavior. As the strain increased, both G' and G" decreased and they eventually intersected at a crossover strain (51.9%). Beyond the crossover strain, the G" exceeded G', indicating a dominant viscous response. The recovery of the hydrogel moduli under alternating high (100%) and low strain (0.1%) was also tested (FIG. 3B). At high strains, both G' and G" significantly decreased. At low strains, both G' and G" increased and were able to recover around 86% of its original value. This demonstrated the capability of the hydrogel to recover its stability and integrity after injection. Furthermore, the viscosity of the hydrogel decreased as the shear rate increased, demonstrating its shear-thinning behavior before in situ covalent crosslinking (FIG. 3C). G' and G" as a function of frequency are shown in FIG. 3D. It can be observed that G'>G", indicating viscoelastic solid-like behavior.

Figure 3E:
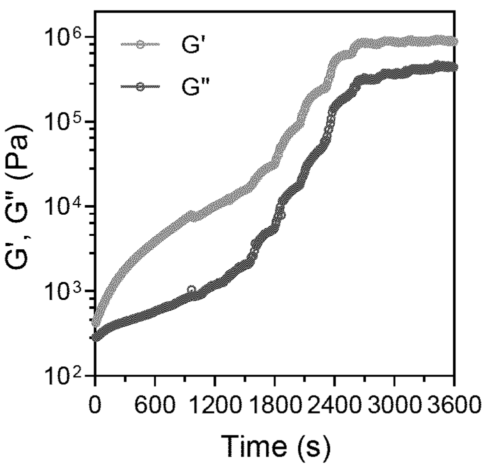
Figure 3F:
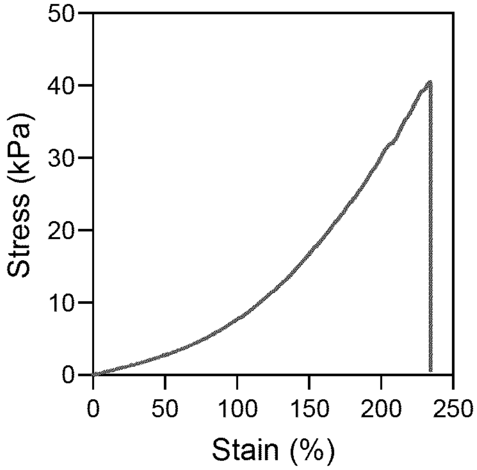
Figure 3G:
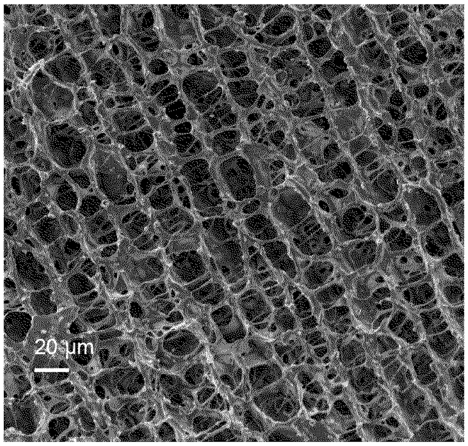
Figure 3H:
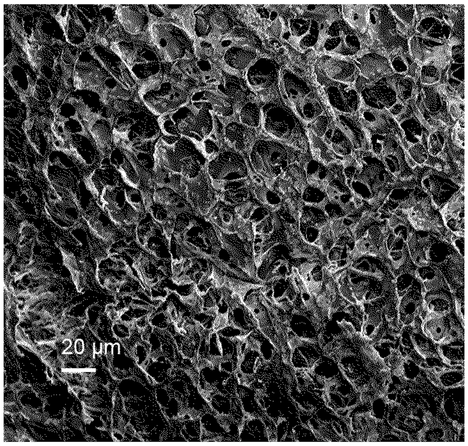

To study the in situ covalent crosslinking reaction, the real-time rheological performance of the DCN hydrogel undergoing the thiol-ene reaction was monitored by measuring the variation in its moduli at 37° C. (FIG. 3E). Both the storage (G') and loss moduli (G") of the DCN hydrogel were gradually increased over time, indicating continuous in situ secondary crosslinking mediated by the thiol-ene reactions between the thiol groups on DTT and methacrylate groups on Alg-MA and CMC-MA. After ~45 min, increments of G' and G" both reached plateaus indicating complete thiol-ene reactions. The stress-strain curve of in situ covalently crosslinked DCN hydrogel was studied by a mechanical tester (FIG. 3F). The DCN hydrogel had a Young's modulus of ~5.7 kPa with 234% elongation at break. The microstructure of the DCN hydrogel before and after in situ covalent crosslinking was observed by scanning electron microscopy (SEM) using lyophilized DCN hydrogel samples (FIGS. 3G, 3H). Observable topological and morphological changes including reduced mesh sizes and thickened polymer fibers were noted under SEM, as a result of in situ covalent crosslinking.

Example 3—Effects of Hydrogels on Cell Viability

Cell viability: To study the cell viability of the various hydrogel components, NIH 3T3 fibroblasts were seeded in 96-well plates (10,000 cells per well) in 100 μL of cell culture media 24 h prior to treatments. On the day of treatments, Alg-MA, CMC-MA, and $CaSO_4{\cdot}2H_2O$ dissolved/suspended in PBS were added to the cells at different concentrations, respectively. After 1 day of incubation, Cell Counting Kit-8 (CCK-8, Dojindo Molecular Technologies, Inc.) was used to quantify cell viability following the manufacturer's protocol, and the cells were further incubated at 37° C. for 48 h. Thereafter, the absorbance of culture media in each well was measured at 450 nm using a microplate reader system (Promega Corporation), and the average absorbance and percentage of cell viability were calculated.

For hydrogel samples, 50 μL of the DCN hydrogel was first injected to the bottom of a well in a 96-well plate. The plate was then centrifuged at 300×g for 10 min to ensure even distribution of hydrogel at the well bottom, and the DCN hydrogel was fully crosslinked at 37° C. overnight in an incubator. Then, 10 uL of neutralized human whole blood was added to the top surface of the hydrogel. After blood clotted, the hydrogel surface was thoroughly rinsed with DPBS 1×. Cell seeding and CCK-8 treatments were carried out following the same procedures described above. The supernatant of cell culture media in the hydrogel-coated well was transferred to an empty well and subsequently, the absorbance at 450 nm was measured using a microplate reader system (Promega Corporation).

Figure 4A:
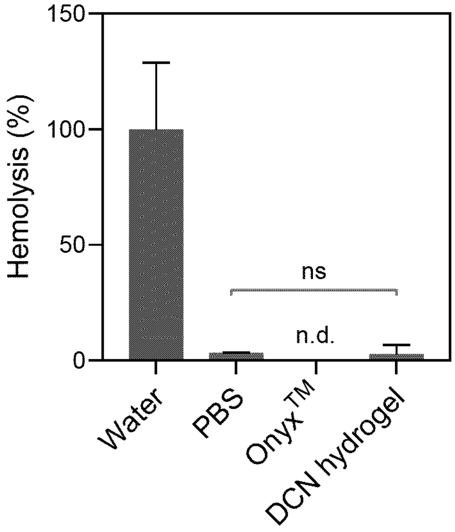
FIGS. 4A-4D show the hemostasis, hemolysis, radiopacity and biocompatibility of an illustrative embodiment of the present compositions (referred to as a "DCN hydrogel").
Figure 4B:
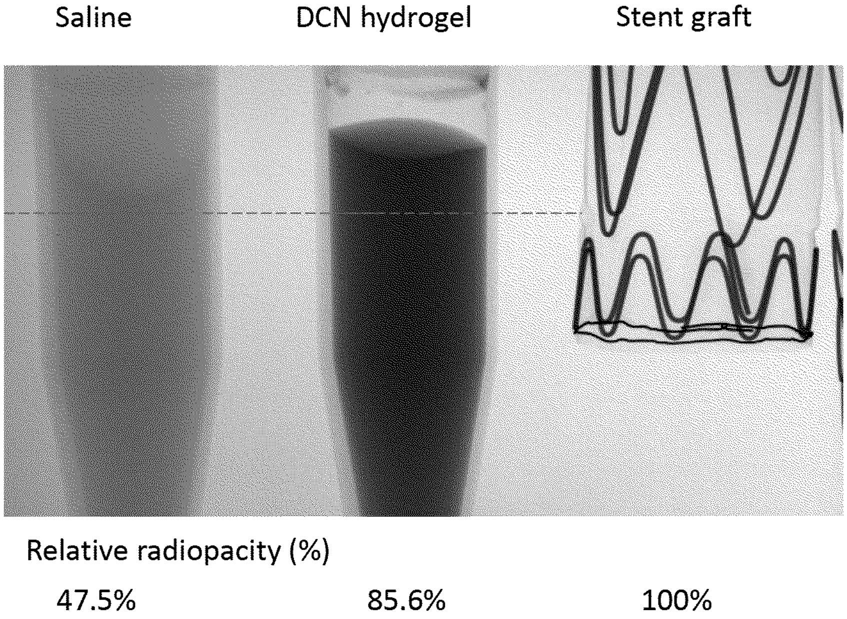
Figure 4C:
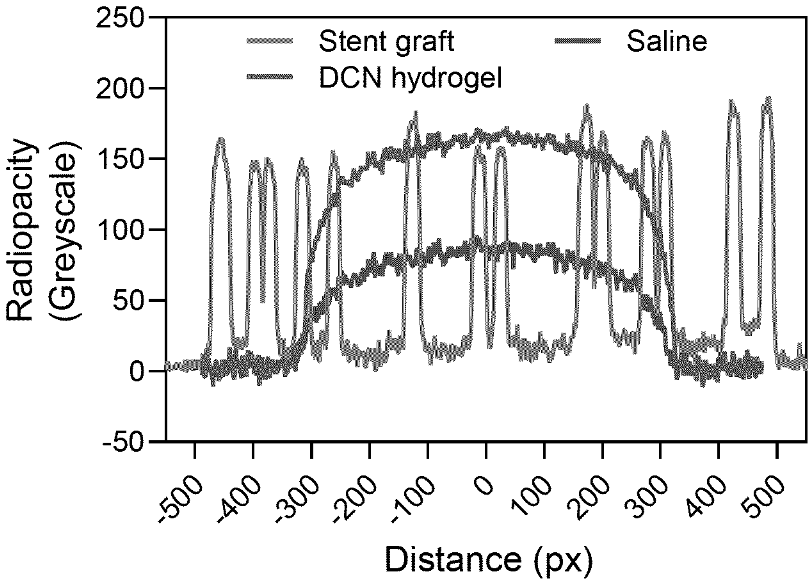
Figure 4D:
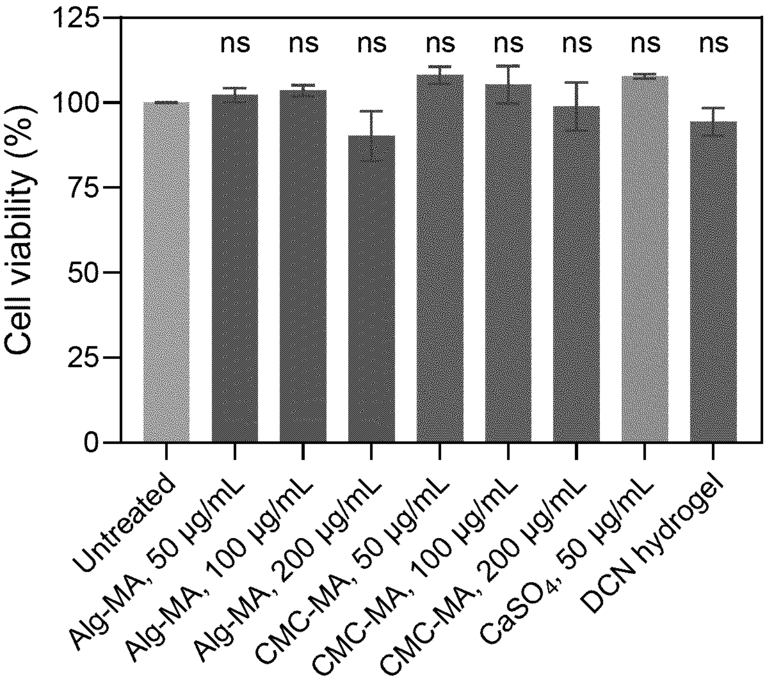

The in vitro biocompatibility of the DCN hydrogel was assessed in vitro using NIH 3T3 fibroblast cells and cell counting kit-8 (CCK-8) (FIG. 4D). Cells treated with solutions of Alg-MA, CMC-MA, or $CaSO_4$ did not show any significant reduction in cell viability. Cells seeded and cultured on the plate coated with covalently crosslinked DCN hydrogel did not exhibit any sign of cytotoxicity either, indicating excellent biocompatibility of DCN hydrogel.

Example 4—Hydrogel Hemostasis and Hemolysis Activity

TNF-α assay: RAW264.7 macrophages were seeded 24 h prior to treatments in 96-well plates at 10,000 cells per well with or without hydrogel-coated wells, following the aforementioned protocol. On the day of treatments, ALG-MA (200 μg/mL), CMC-MA (200 μg/mL), and $CaSO_4{\cdot}2H_2O$ (50 μg/mL) dissolved or suspended in PBS were added to the cell culture media, respectively. After 24 h of incubation, the cell culture media were collected. TNF-α level in the culture media was analyzed using an enzyme-linked immunosorbent assay (ELISA, R&D Systems, MTA00B) following the manufacturer's protocol.

In vitro hemostasis test: The hemostasis test was conducted based on a previously reported protocol with some modifications[20]. Human whole blood containing sodium citrate (16.65 mM) as an anticoagulant was used for this study. The citrated blood was neutralized by mixing the blood with $CaCl_2$ solution (224.79 mM) at a 9/1 (vol/vol) ratio. The mixture was then vortexed for 10 s right before the test. Thereafter, 0.12 mL of the neutralized blood and 0.04 ml of the samples (for the saline, DCN hydrogel and Onyx groups) or 0.04 $cm^3$ metallic coils (diameter=2 mm, length=12.7 mm, Boston Scientific Interlock™ Fibered IDC™, 2 mm/4 cm) were added into the wells in a 96-well plate. At different time points after treatments, the supernatant in each well was aspirated and the well was rinsed with PBS three times. The remaining blood clots, adhering to the bottom of the well, were then observed to evaluate the hemostatic capability of each group.

In vitro hemolysis test: Red blood cells were separated from the human whole blood by centrifugation at 2,500 rpm for 10 min. The separated cells were washed with PBS three times and re-suspended in PBS. For testing the hemolysis of materials, 0.1 mL of the cell suspension was mixed with 0.2 mL of ultrapure water, PBS, Onyx, and DCN hydrogel, respectively. The mixture was then incubated at 37° C. for 3 h. The supernatant was collected by centrifugation at 2,500 rpm for 10 min and mixed with Drabkin's reagent at a ratio of 1/1 (vol/vol). Thereafter, the absorbance at 540 nm was measure by UV-Vis spectrometer and the hemolysis rate was finally calculated as:

$$\text{Hemolysis}(\%) = \frac{\text{Absorbance(Sample)} - \text{Absorbance}(PBS)}{\text{Absorbance(Ultrapure water)} - \text{Absorbance}(PBS)} \times 100\%$$

Radiopacity study: The radiopacity of the DCN hydrogel was studied using X-ray inspection system μnRay 7600f (Matsusada Precision Inc.) with an output voltage at 90 kV and power at 18 W. Physiological saline and an abdominal metallic stent graft (GORE® EXCLUDER® AAA Endoprosthesis, W. L. Gore & Associates, Inc.) were used as references.

Discussion. The hemostatic capability of the DCN hydrogel was evaluated by monitoring the clotting time of human whole blood after contact with DCN hydrogel surfaces in a 96-well plate. Notably, blood treated with the DCN hydrogel clotted within the first minute upon contact, while blood treated with physiological saline (0.9% NaCl) was clotted after 6 minutes. The hemostatic capability of the DCN hydrogel was further compared with clinically applied embolic agents for endovascular embolization, including Onyx™, an FDA-approved dimethyl sulfoxide solution of ethylene vinyl-alcohol copolymer with micronized tantalum powder, and metallic coils. Onyx™ did not induce any observable hemostasis, due to its lack of components for hemostasis cascade activation. Metallic coils, on the other hand, successfully induced blood coagulation within 2 minutes after treatment, taking a longer time than the DCN hydrogel. In addition, the DCN hydrogel and Onyx™ did not induce hemolysis of red blood cells, in comparison with ultrapure water (positive control) and saline (negative control) (FIG. 4A).

Radiopacity is an important property for embolic materials because endovascular surgery requires X-ray imaging for real-time tracking for accurate deployment and preventing dangerous non-target embolization.[8c] Iohexol (product name: Omnipaque™), an FDA-approved and currently clinically used water-soluble contrast agent for X-ray imaging, was chosen and mixed in the DCN hydrogel, because it does not possess reactive groups which could interfere the thiol-ene reaction for in situ covalent crosslinking. The radiopacity of the DCN hydrogel was then evaluated by an X-ray inspection system. Under X-ray, the DCN hydrogel exhibited 85.6% radiopacity relative to the abdominal stent graft (FIG. 4B), as quantified by the greyscale of the pixels in the X-ray imaging (FIG. 4C).

Example—In Vivo Embolization with Hydrogels

In vivo femoral arterial embolization in a rabbit model: On the day of treatments, rabbits were intravenously injected with Vetorphale (0.5 mg/kg) for pain-relief. The anesthesia was initiated through animal anesthesia mask with 4%-5% isoflurane and maintained through tracheal intubation with 2%-3% isoflurane. The neck and thigh of the animal were shaved, fixed, and disinfected. Thereafter, the animal was transfused with Ringer's lactate solution through auricular vein (1 droplet/2 s) and intravenously injected with heparin (150 units/kg). For material injections, the femoral artery of the animal was first exposed, and the blood flow was stopped by clipping the distal position of the artery. Saline, Onyx or DCN hydrogel was then injected, respectively. After certain time points (i.e., 1 day, 1 week and 1 month), autopsy of the animal was performed. The animal was intravenously injected with Vetorphale and anesthetized by isoflurane as aforementioned. The left ventricle was thoracotomically punctured and circulated with physiological saline and 4% paraformaldehyde, respectively. The treated artery was then collected and preserved in 4% paraformaldehyde for histological analysis.

Histology Studies: Artery samples were embedded into paraffin blocks, sectioned, and stained with hematoxylin and eosin (H&E) and Masson's trichrome, respectively. For immunohistochemical staining, macrophages were stained with primary antibodies (MAC387, Abcam, ab22506) and secondary antibodies (Nichirei Biosciences, 414171). Proliferating cells were stained with primary antibodies (PCNA, Dako, M0879) and secondary antibodies (Nichirei Biosciences, 414171). Apoptotic cells were stained with ApopTag® Peroxidase In Situ Apoptosis Detection Kit (Sigma-Aldrich, S7100). All staining procedures followed the manufacturers' protocols.

Figure 5A:
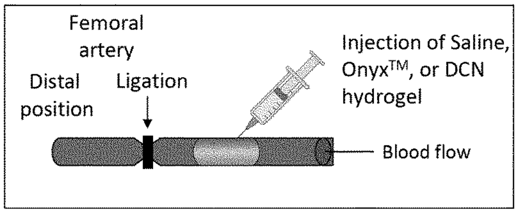
FIGS. 5A-5D show H&E and Masson's trichrome staining results of embolized rabbit arteries.
Figure 5B:
Figure 5C:
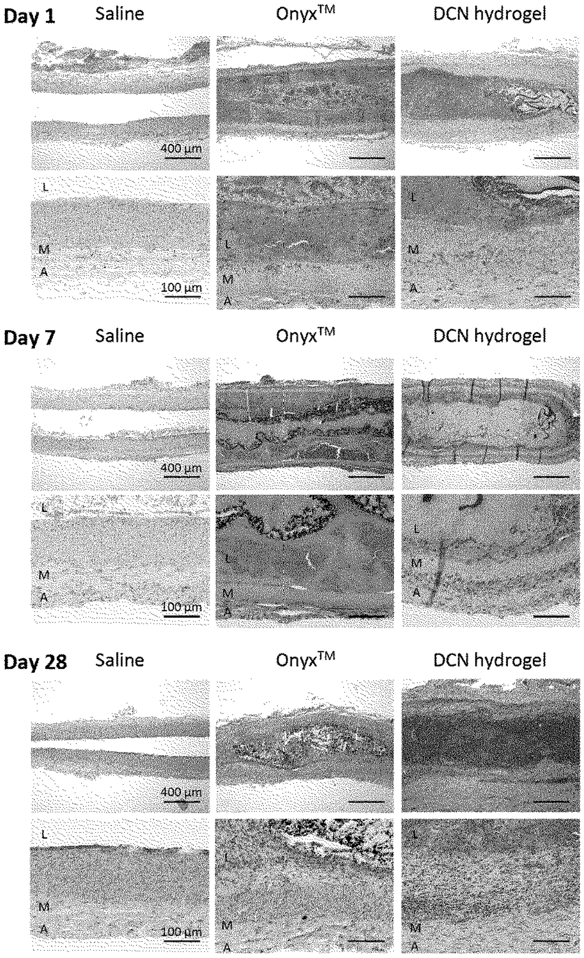
Figure 5D:
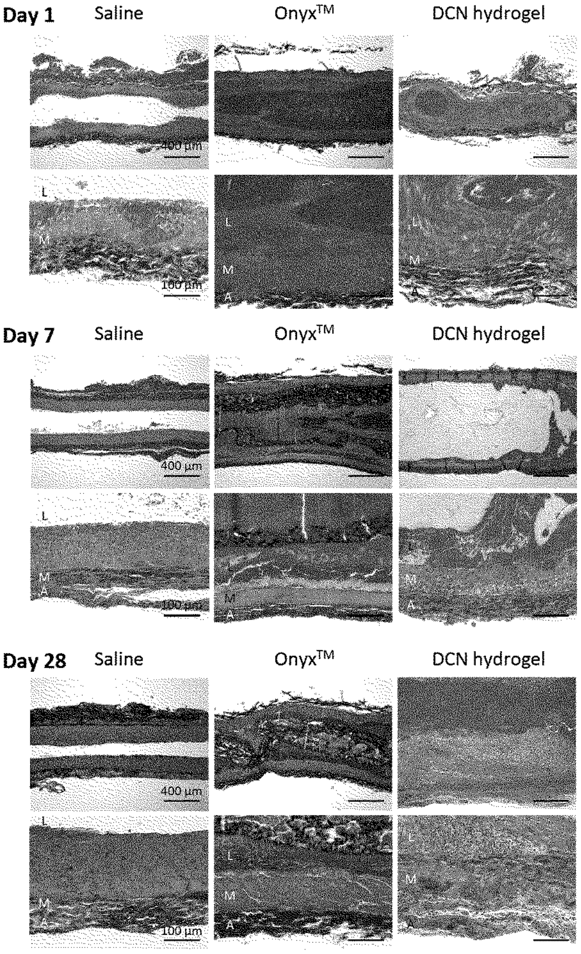

Discussion. The in vivo endovascular embolization efficacy of the DCN hydrogel was tested in a rabbit model. The femoral artery of rabbit (n=3) was embolized by the DCN hydrogel, Onyx™, and saline as a control, respectively (FIGS. 5A and 5B). The efficacy of arterial occlusion was analyzed 1, 7, and 28 days after surgery. The morphological character of the treated artery was assessed by H&E staining and Masson's trichrome staining (FIGS. 5C and 5D, Tables 1 and 2).

TABLE 1

Assessment of the H&E staining results

| | Group | | | | | | | | |
|---|---|---|---|---|---|---|---|---|---|
| | Saline | | | Onyx ™ | | | DCN hydrogel | | |
| Period | Day 1 | Day 7 | Day 28 | Day 1 | Day 7 | Day 28 | Day 1 | Day 7 | Day 28 |
| Blood clotting | 3 | 0 | 0 | 3 | 3 | 0 | 3 | 3 | 0 |
| Organized thrombus | 0 | 1 | 3 | 0 | 0 | 3 | 0 | 1 | 3 |
| Collection/infiltration of pseudo-eosinophil | 1 | 0 | 0 | 2 | 1 | 1 | 2 | 2 | 1 |

TABLE 1-continued

| Assessment of the H&E staining results | | | | | | | | | |
|---|---|---|---|---|---|---|---|---|---|
| | Group | | | | | | | | |
| | Saline | | | Onyx ™ | | | DCN hydrogel | | |
| Period | Day 1 | Day 7 | Day 28 | Day 1 | Day 7 | Day 28 | Day 1 | Day 7 | Day 28 |
| Lymphocyte infiltration | 0 | 0 | 1 | 0 | 1 | 1 | 0 | 0 | 3 |
| Increasing macrophage | 0 | 1 | 1 | 0 | 0 | 3 | 0 | 2 | 3 |
| Foreign body giant cells | 0 | 0 | 0 | 0 | 0 | 3 | 0 | 0 | 2 |
| Necrosis of vessel wall | 2 | 0 | 0 | 3 | 3 | 0 | 1 | 2 | 0 |
| Cell debris | 0 | 0 | 0 | 2 | 1 | 0 | 0 | 0 | 3 |
| Fibrous tissue proliferation (fibrosis), thickening of vessel wall | 0 | 3 | 3 | 0 | 0 | 1 | 0 | 0 | 3 |

0: none;
1: mild;
2: moderate;
3: high

TABLE 2

| Assessment of the Masson's trichrome staining results | | | | | | | | | |
|---|---|---|---|---|---|---|---|---|---|
| | Group | | | | | | | | |
| | Saline | | | Onyx ™ | | | DCN hydrogel | | |
| Period | Day 1 | Day 7 | Day 28 | Day 1 | Day 7 | Day 28 | Day 1 | Day 7 | Day 28 |
| Fibrous tissue proliferation (fibrosis), thickening of vessel wall | 0 | 4 | 4 | 0 | 1 | 3 | 0 | 2 | 4 |

0: none;
1: slight;
2: mild;
3: moderate;
4: high

Onyx™ appeared as black color in both the H&E and Masson's trichrome staining images while the DCN hydrogel appeared as light purple color in the H&E staining images and light blue color in the Masson's trichrome staining images. Both Onyx™ and the DCN hydrogel induced complete occlusion of the targeted artery on Day 1, 7, and 28. On Day 1, both Onyx™ and the DCN hydrogel showed luminal occlusion with associated thrombosis (FIG. 5C), while the saline group showed patency of the lumen. Moreover, Masson's trichrome staining indicated minimal to no fibrosis within the occluded lumen in both Onyx™ and DCN hydrogel groups (FIG. 5D). On Day 7, sustained thrombosis of the lumen was induced in both Onyx™- and DCN hydrogel-treated arteries, whereas patency of the lumen was found in the saline group. On Day 28, more fibrotic changes were found in the DCN hydrogel-treated artery than the Onyx™-treated one, which indicate the transition from material-based occlusion to fibrotic occlusion of the arterial lumen after 28 days. In contrast, the saline group exhibited patency of the lumen with marked intimal hyperplasia.

Figure 6:
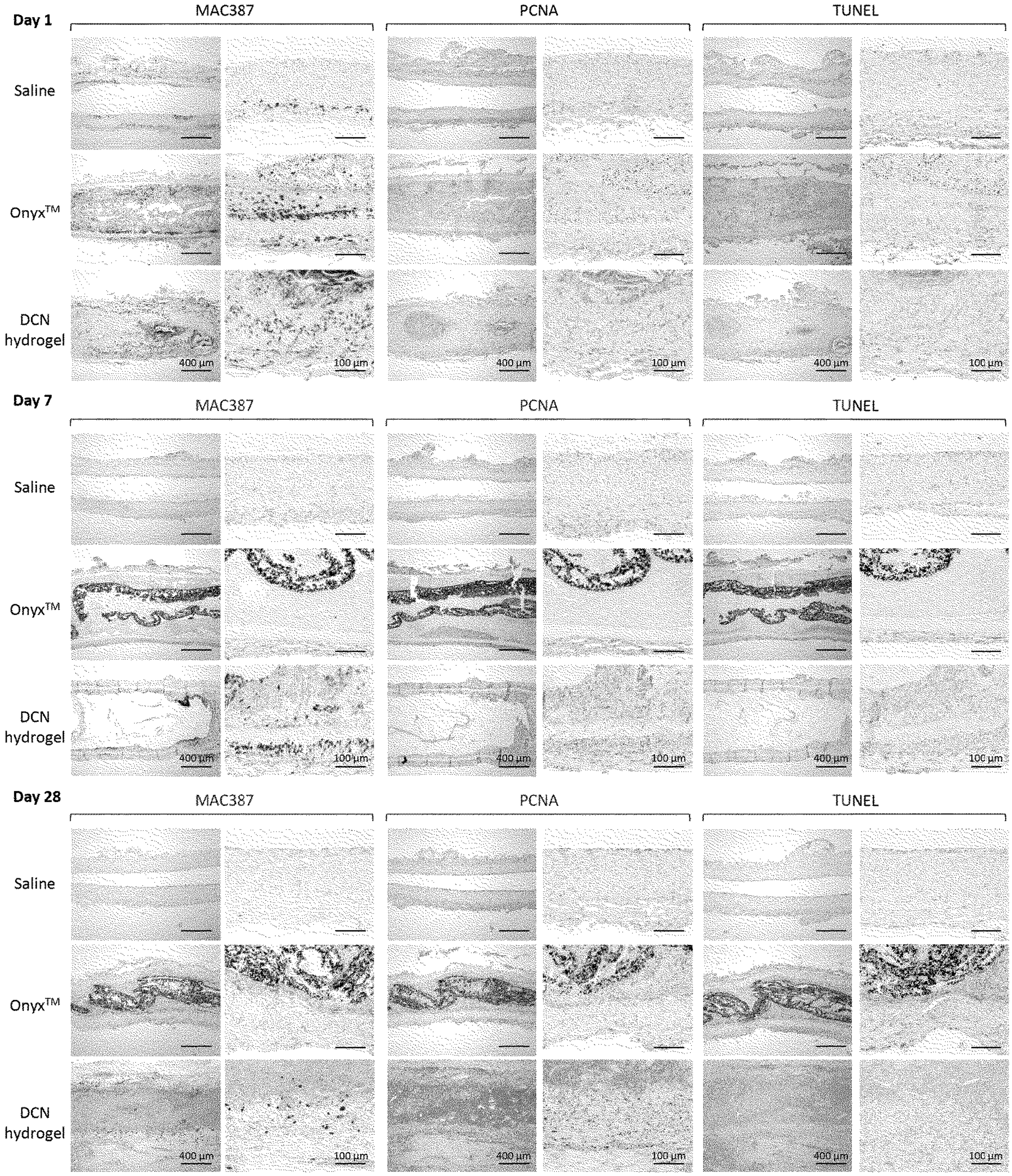

Immunohistochemical analyses of the treated arteries are shown in FIG. 6 and Table 3. Inflammatory changes, cell proliferation, and cell apoptosis were analyzed by immunohistochemical staining of MAC387, PCNA, and TUNEL, respectively (n=3). Acute inflammation was found in both Onyx™ and DCN hydrogel groups on Day 1 and Day 7, but the inflammatory response was decreased on Day 28. The activation of macrophages by the DCN hydrogel can be attributed to the polysaccharide components, as indicated by an in vitro study of TNFa activation (results not shown). Proliferative changes in the DCN hydrogel group were seen on Day 7 and Day 28, with cellular component-based luminal occlusion. In contrast, in the Onyx™ group, luminal occlusion was mostly induced by the embolic material itself, with minimal cellular components observed. TUNEL staining demonstrated similar apoptotic activity in the medial and adventitial layers in all three groups on Day 1 and Day 7. On Day 28, apoptotic activities were similar in the saline and Onyx™ group but were decreased to almost none in the DCN hydrogel group.

TABLE 3

Assessment of the immunohistochemistry staining results

| | Group | | | | | | | | |
|---|---|---|---|---|---|---|---|---|---|
| | Saline | | | Onyx ™ | | | DCN hydrogel | | |
| Period | Day 1 | Day 7 | Day 28 | Day 1 | Day 7 | Day 28 | Day 1 | Day 7 | Day 28 |
| MAC387, macrophage | 3 | 1 | 0 | 4 | 3 | 0 | 4 | 3 | 2 |
| PCNA, proliferating cells | 1 | 1 | 1 | 2 | 3 | 3 | 2 | 2 | 3 |
| TUNEL, apoptotic cells | 1 | 1 | 1 | 0 | 0 | 0 | 1 | 0 | 0 |

0: none;
1: slight;
2: mild;
3: moderate;
4: high

Collectively, the DCN hydrogel group showed acute occlusion of the treated artery and induced a continuous increase in collagen with cellular proliferation, which are histological characteristics of the luminal occlusion/narrowing by the intimal hyperplasia of the artery.[14] In the clinical setting, recanalization of the treated artery and aneurysm is a major concern,[15] especially after the endovascular treatment of the large artery, like an aortic aneurysm.[16] The DCN hydrogel group showed both acute thrombosis of the targeted artery and delayed fibrotic changes with continued occlusion by the cellular component. At a later stage, successful embolization was achieved and maintained mostly by fibrous tissue, not by the DCN hydrogel. Together with the injectability and in situ covalent crosslinking capability of the DCN hydrogel which enables its deployment in the target artery including large cavity without the fear of distal micro-embolization of catheter entrapment, the DCN hydrogel is promising to be used as a preferred material for vascular embolization.

REFERENCES

[1] a) A. England, R. Mc Williams, *Ulster Med. J.* 2013, 82, 3; b) K. C. Kent, *N. Engl. J. Med.* 2014, 371, 2101.

[2] a) J. E. Lopera, *Semin. Interv. Radiol.* 2010, 27, 014; b) S. Vaidya, K. R. Tozer, J. Chen, *Semin. Interv. Radiol.* 2008, 25, 204.

[3] J. Hu, H. Albadawi, B. W. Chong, A. R. Deipolyi, R. A. Sheth, A. Khademhosseini, R. Oklu, *Adv. Mater.* 2019, 31, e1901071.

[4] R. K. Avery, H. Albadawi, M. Akbari, Y. S. Zhang, M. J. Duggan, D. V. Sahani, B. D. Olsen, A. Khademhosseini, R. Oklu, *Sci. Transl. Med.* 2016, 8, 365ra156.

[5] a) Q. Guo, J. Zhao, Y. Ma, B. Huang, D. Yuan, Y. Yang, X. Du, *J. Vasc. Surg.* 2020, 71, 1029; b) Q. Li, P. Hou, *J. Endovasc. Ther.* 2020, 27, 109; c) C. Mascoli, A. Freyrie, M. Gargiulo, E. Gallitto, R. Pini, G. Faggioli, C. Serra, C. De Molo, A. Stella, *Eur. J. Vasc. Endovasc. Surg.* 2016, 51, 632; d) C. Marcelin, Y. Le Bras, F. Petitpierre, D. Midy, E. Ducasse, N. Grenier, F. Cornelis, *Diagn. Interv. Imaging* 2017, 98, 491.

[6] G. Calugi, W. Dorigo, A. Capone, D. Esposito, E. Giacomelli, C. Pratesi, *J. Surg. Case Rep.* 2021, 2021, rjab231.

[7] A. Arat, B. E. Cil, I. Vargel, B. Turkbey, M. Canyigit, B. Peynircioglu, Y. O. Arat, *AJNR Am. J. Neuroradiol.* 2007, 28, 1409.

[8] a) B. Liu, Z. Xu, H. Gao, C. Fan, G. Ma, D. Zhang, M. Xiao, B. Zhang, Y. Yang, C. Cui, T. Wu, X. Feng, W. Liu, *Adv. Funct. Mater.* 2020, 30, 1910197; b) L. Fan, M. Duan, Z. Xie, K. Pan, X. Wang, X. Sun, Q. Wang, W. Rao, J. Liu, *Small* 2020, 16, e1903421; c) J. Hu, I. Altun, Z. Zhang, H. Albadawi, M. A. Salomao, J. L. Mayer, L. Hemachandra, S. Rehman, R. Oklu, *Adv. Mater.* 2020, 32, e2002611; d) H. Albadawi, I. Altun, J. Hu, Z. Zhang, A. Panda, H. J. Kim, A. Khademhosseini, R. Oklu, *Adv. Sci.* 2020, 8, 2003327; e) I. Altun, J. Hu, H. Albadawi, Z. Zhang, M. A. Salomao, J. L. Mayer, L. Jamal, R. Oklu, *Adv. Mater.* 2020, 32, e2005603.

[9] a) C. B. Rodell, J. W. MacArthur, S. M. Dorsey, R. J. Wade, L. L. Wang, Y. J. Woo, J. A. Burdick, *Adv. Funct. Mater.* 2015, 25, 636; b) C. B. Rodell, N. N. Dusaj, C. B. Highley, J. A. Burdick, *Adv. Mater.* 2016, 28, 8419.

[10] J.-Y. Sun, X. Zhao, W. R. K. Illeperuma, O. Chaudhuri, K. H. Oh, D. J. Mooney, J. J. Vlassak, Z. Suo, *Nature* 2012, 489, 133.

[11] A. B. Lowe, *Polym. Chem.* 2010, 1, 17.

[12] M. H. Chen, L. L. Wang, J. J. Chung, Y.-H. Kim, P. Atluri, J. A. Burdick, *ACS Biomater. Sci. Eng.* 2017, 3, 3146.

[13] E. Sanfins, C. Augustsson, B. Dahlback, S. Linse, T. Cedervall, *Nano Lett.* 2014, 14, 4736.

[14] a) S. Franco, A. Stranz, F. Ljumani, G. Urabe, M. Chaudhary, D. Stewart, V. S. Pilli, M. Kelly, D. Yamanouchi, K. C. Kent, B. Liu, *Heliyon.* 2020, 6, e04028; b) D. Yamanouchi, H. Banno, M. Nakayama, M. Sugimoto, H. Fujita, M. Kobayashi, H. Kuwano, K. Komori, *J. Vasc. Surg.* 2005, 42, 757; c) J. Shen, J. B. Song, J. Fan, Z. Zhang, Z. J. Yi, S. Bai, X. L. Mu, Y. B. Yang, L. Xiao, *Eur. J. Vasc. Endovasc. Surg.* 2021, 61, 648.

[15] a) I. Rezek, G. Mousan, Z. Wang, M. H. Murad, D. F. Kallmes, *AJNR Am. J. Neuroradiol.* 2013, 34, 1769; b) Z. Serafin, P. Strześniewski, W. Lasek, W. Beuth, *Neurol. Neurochir. Pol.* 2011, 45, 421.

[16] Q. Guo, X. Du, J. Zhao, Y. Ma, B. Huang, D. Yuan, Y. Yang, G. Zeng, F. Xiong, *PLoS One* 2017, 12, e0170600.

[17] L. He, E. S. Read, S. P. Armes, D. J. Adams, *Macromolecules* 2007, 40, 4429.

[18] O. Jeon, K. H. Bouhadir, J. M. Mansour, E. Alsberg, *Biomaterials* 2009, 30, 2724.

[19] C. Loebel, C. B. Rodell, M. H. Chen, J. A. Burdick, *Nat. Protoc.* 2017, 12, 1521.

[20] A. K. Gaharwar, R. K. Avery, A. Assmann, A. Paul, G. H. McKinley, A. Khademhosseini, B. D. Olsen, *Acs Nano* 2014, 8, 9833.

EQUIVALENTS

While certain embodiments have been illustrated and described, a person with ordinary skill in the art, after reading the foregoing specification, can effect changes, substitutions of equivalents and other types of alterations to the methods and oligosaccharides of the present technology or derivatives, nutraceutical compositions, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conditions, starting materials, reagents, compounds, or compositions, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the phrase "consisting essentially of" will be understood to include those elements specifically recited and those additional elements that do not materially affect the basic and novel characteristics of the claimed technology. The phrase "consisting of" excludes any element not specified. The terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. More specifically, it will be understood that each use of terms such as "comprising," "consisting essentially of," or "consisting of", discloses and provides written description and support for the use any of the other terms with the same or any other embodiment described herein.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein. Thus, for example, a group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A composition comprising a mixture of a source of calcium ions, alginate conjugated to an acrylate monomer (ALG-A), carboxymethylcellulose conjugated to an acrylate monomer (CMC-A) and water, wherein the mixture is a shear-thinning gel, and wherein the composition comprises 0.1 wt % to 10 wt % of a source of calcium ions.

2. The composition of claim 1, wherein the source of calcium ions is calcium sulfate, calcium chloride, calcium acetate, calcium gluconate, calcium citrate, or calcium lactate, or a mixture of any two or more thereof.

3. The composition of claim 1, comprising 0.5 wt % to 10 wt % ALG-A.

4. The composition of claim 3, comprising 2 wt % to 6 wt % ALG-A.

5. The composition of claim 1, comprising 0.5 wt % to 20 wt % CMC-A.

6. The composition of claim 1, wherein the acrylate monomer of ALG-A, CMC-A or both comprises acrylate or methacrylate.

7. The composition of claim 6, wherein the acrylate monomer of ALG-A, CMC-A or both comprises an aminoalkyl acrylate or aminoalkyl methacrylate.

8. The composition of claim 7, wherein the acrylate monomer of ALG-A, CMC-A or both is 2-aminoethylacrylate or 2-aminoethylmethacrylate.

9. The composition of claim 1, wherein the weight ratio of ALG-A:CMC-A ranges from 1:2 to 2:1.

10. The composition of claim 1, further comprising a polythiol agent.

11. The composition of claim 10, wherein the polythiol agent is a dithiol, trithiol or tetrathiol agent.

12. The composition of claim 10, wherein the polythiol agent is selected from the group consisting of dithiothreitol, dithioerythritol, propane-1,3-dithiol, meso-2,3-dimercapto-succinic acid, dimercaprol, dihydrolipoic acid, trimethylol-propane tris(3-mercaptopropionate), pentaerythritol tetrakis (3-mercaptopropionate), poly(ethylene glycol) with two terminal thiols, and 4-arm poly(ethylene glycol) with four terminal thiols.

13. The composition of claim 10, comprising 0.1 to 2 molar equivalents of thiol groups on the polythiol agent to acrylate groups on ALG-A.

14. The composition of claim 1 further comprising a thiol-ene crosslinking catalyst.

15. The composition of claim 14 wherein the thiol-ene crosslinking catalyst is tris(2-carboxyethyl) phosphine.

16. The composition of claim 14 comprising 0.1 mM to 100 mM thiol-ene crosslinking catalyst.

17. A composition comprising a crosslinked hydrogel resulting from the compositions of claim 1.

18. The composition of claim 1, wherein the composition exhibits a viscosity of at least 1,000 Pa·s at a shear rate of 0.1/s.

19. The composition of claim 18, wherein the composition exhibits a viscosity of at least 10,000 Pa·s at a shear rate of 0.1/s.

20. The composition of claim 1, wherein the composition exhibits a viscosity of less than 100 Pa·s at a shear rate of 20/s.

21. The composition of claim 20, wherein the composition exhibits a viscosity of less than 20 Pas at a shear rate of 20/s.

22. The composition of claim 1, wherein the composition exhibits a storage modulus (G') greater than the loss modulus (G") at strains of less than 50% when measured at a fixed frequency of 0.1 Hz and a temperature of 37° C.

23. The composition of claim 1, wherein the composition exhibits a Young's modulus of about 4 kPa to about 8 kPa.

24. A method of making a composition comprising mixing alginate conjugated to an acrylate monomer (ALG-A), carboxymethylcellulose conjugated to an acrylate monomer (CMC-A) and a source of calcium ions in water to provide a shear-thinning gel, wherein the composition comprises 0.1 wt % to 10 wt % of a source of calcium ions.

25. The method of claim 24, further comprising mixing a polythiol, and optionally a thiol-ene crosslinking catalyst, with ALG-A, CMC-A and the source of calcium ions in water.

26. A method of treatment comprising administering an effective amount of a composition of claim 10 to a subject in need thereof, wherein the method is for the treatment of internal bleeding, aneurysm, and/or vascular malformation.

27. The method of claim 26, wherein the subject is human.

28. The method of claim 27, wherein the subject is suffering from one or more of internal bleeding, aneurysm, and vascular malformation.

* * * * *